United States Patent
Delfosse et al.

(10) Patent No.: US 7,244,274 B2
(45) Date of Patent: Jul. 17, 2007

(54) JOINT PROSTHESIS

(75) Inventors: Daniel Delfosse, Bern (CH); Walter Supper, Bettlach (CH); Beat Grunder, Worb (CH)

(73) Assignee: Mathys Medizinaltechnik AG, Bettlach (CH)

( * ) Notice: Subject to any disclaimer, the term of this patent is extended or adjusted under 35 U.S.C. 154(b) by 563 days.

(21) Appl. No.: 10/468,239

(22) PCT Filed: Feb. 25, 2002

(86) PCT No.: PCT/EP02/01969

§ 371 (c)(1),
(2), (4) Date: Aug. 18, 2003

(87) PCT Pub. No.: WO02/069852

PCT Pub. Date: Sep. 12, 2002

(65) Prior Publication Data

US 2004/0220677 A1    Nov. 4, 2004

(30) Foreign Application Priority Data

Mar. 1, 2001   (DE) ............................... 101 09 804

(51) Int. Cl.
*A61F 2/38* (2006.01)
(52) U.S. Cl. ................................................. 623/20.33
(58) Field of Classification Search ............. 623/20.33, 623/20.32, 20.34, 20.14, 20.15, 20.21, 20.24, 623/20.28, 20.29, 23.17, 23.44, 23.46, 17.13
See application file for complete search history.

(56) References Cited

U.S. PATENT DOCUMENTS

| 4,136,405 A | * | 1/1979 | Pastrick et al. | ......... 623/20.25 |
|---|---|---|---|---|
| 4,673,407 A | * | 6/1987 | Martin | ..................... 623/20.33 |
| 4,728,332 A | * | 3/1988 | Albrektsson | ............. 623/20.29 |
| 4,950,297 A | * | 8/1990 | Elloy et al. | ............... 623/20.29 |
| 5,080,675 A | * | 1/1992 | Lawes et al. | ............ 623/20.33 |
| 5,344,460 A | * | 9/1994 | Turanyi et al. | .......... 623/20.33 |
| 5,549,689 A | | 8/1996 | Epstein et al. | |
| 5,782,925 A | | 7/1998 | Collazo et al. | |

(Continued)

FOREIGN PATENT DOCUMENTS

DE   2810748 A   3/1978

(Continued)

*Primary Examiner*—Eduardo C. Robert
*Assistant Examiner*—David Comstock
(74) *Attorney, Agent, or Firm*—Scully, Scott, Murphy & Presser, P.C.

(57) ABSTRACT

The invention relates to a joint prosthesis, especially a knee joint prosthesis, for establishing an articulated connection between a first bone and at least one second bone. The inventive prosthesis comprises a first component (1) that is at least indirectly linked with the first bone, at least one second component (2) on which the second bone at least indirectly supports itself and which is movably mounted on at least one bearing surface (22) of the first component (1), and a connecting element (4) that interlinks the first component (1) with the second component (2). The connecting element (4) comprises an elastically deformable element (5) that facilitates a deflection of the first component (1) relative to the second component (2) from an initial position. When the first component (1) is deflected, the elastically deformable element (5) generates a restoring force that acts upon the first component (1) and restores the first component (1) to the initial position.

6 Claims, 6 Drawing Sheets

U.S. PATENT DOCUMENTS

Figures 1A, 1B:
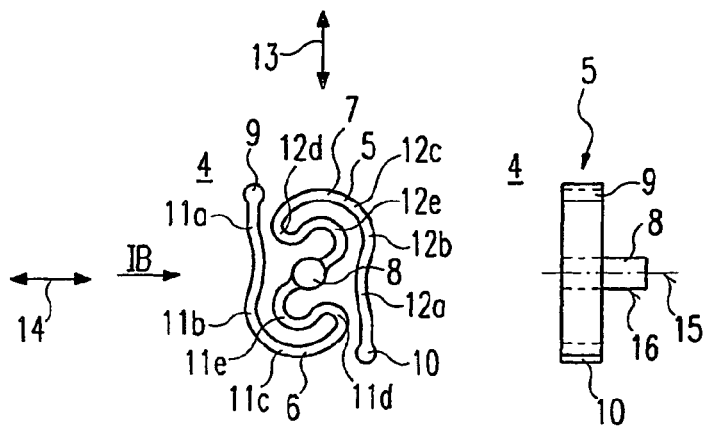

| | | | |
|---|---|---|---|
| 6,090,144 A * | 7/2000 | Letot et al. | 623/20.34 |
| 6,210,444 B1 * | 4/2001 | Webster et al. | 623/20.33 |
| 6,296,666 B1 * | 10/2001 | Gardner | 623/20.29 |
| 6,319,283 B1 * | 11/2001 | Insall et al. | 623/20.33 |
| 6,361,564 B1 * | 3/2002 | Marceaux et al. | 623/20.29 |
| 2001/0003803 A1 * | 6/2001 | Leclercq | 623/20.29 |

FOREIGN PATENT DOCUMENTS

| | | |
|---|---|---|
| DE | 3021443 A1 | 6/1980 |
| DE | 3333815 A1 | 9/1983 |
| DE | 3444001 A1 | 11/1984 |
| DE | 19650816 A1 | 12/1986 |
| DE | 3741488 A | 12/1987 |
| DE | 9110504 U1 | 8/1991 |
| EP | 0510178 B1 | 2/1998 |
| EP | 0916322 A2 | 5/1999 |
| EP | 0916322 A3 | 12/1999 |
| FR | 2707871 A1 | 7/1993 |
| WO | WO 8604808 A1 | 8/1986 |
| WO | WO 92/08424 A | 5/1992 |

* cited by examiner

JOINT PROSTHESIS

The invention relates to a joint prosthesis for establishing an articulated connection between a pair of human or animal bones. The invention relates in particular to a knee joint prosthesis for establishing an articulated connection between a first bone (tibia) and at least one second bone (femur).

From EP 0 510 178 B1 a joint prosthesis having the generic features of claim 1 is known. Said known joint prosthesis takes the form of a knee joint prosthesis for establishing an articulated connection between a first bone (tibia) and a second bone (femur). In said case, there are provided a first component, which is connected to the first bone, and a second component, on which the second bone is supported by means of a support means and which is mounted movably on a bearing surface of the first component. A connection element connected to the first component is further provided, which engages into an oblong hole formed in the second component in order to enable a translational and rotational motion of the second component relative to the first component, wherein the translational motion is limited in anterior-posterior direction by means of inner faces formed in the oblong hole.

The joint prosthesis known from EP 0 510 178 B1 has the drawback that the connection element strikes against the inner faces of the oblong hole, which are part of the second component, thereby resulting in increased wear. As said striking moreover leads to an abrupt halting of the motion that does not occur in the natural sequence of motion of a healthy knee, the knee joint prosthesis in said respect disturbs the sequence of motion.

Furthermore, in patients having an implanted knee joint prosthesis, because of the mostly weak, occasionally considerably atrophied or even damaged ligaments a further drawback of EP 0 510 178 B1 manifests itself. For, to exploit the advantages of the translational mobility of the second component relative to the first component requires strong ligaments, which in dependence upon the angular position of the knee joint predetermine the excursion of the first component relative to the second component that comes closest to the natural sequence of motion. Because this is not the case, the result is a sudden displacement of the first component relative to the second component between the two extreme positions in anterior-posterior direction. The known joint prosthesis may therefore be used only for patients having relatively stable ligaments, wherein in the case of use of the joint prosthesis as a knee joint prosthesis at least the cruciate ligament has to be intact.

The joint prosthesis known from EP 0 510 178 B1 also provides for a limitation of the ability of the first component to rotate relative to the second component. Limitation of the ability to rotate is effected in a corresponding manner to limitation of the translational motion by means of stop faces so that, with regard to the rotational motion, the same drawbacks arise as have already been described for the translational motion.

The underlying object of the invention is to provide a joint prosthesis, with which the motion of the first component relative to the second component, in particular a motion in anterior-posterior direction, is improved and with which in particular an adaptation to the natural sequence of motion of a knee joint is achieved, even when there is impairment of the ligaments supporting the joint prosthesis.

The object is achieved by a joint prosthesis having the features of claim 1. Advantageous developments of the invention are possible by virtue of the measures indicated in the sub-claims.

The joint prosthesis according to the invention has the advantage that an excursion of the first component relative to the second component from an initial position is effected by means of an elastically deformable element, which in dependence upon the excursion generates a restoring force acting upon the first component in order to restore the first component to the initial position, with the result that the motion of the joint prosthesis is damped. Thus, even in the case of weakened or damaged ligaments an adaptation of the sequence of motion by means of the joint prosthesis to the natural sequence of motion is achieved. It is moreover ensured that in the relaxed state the joint prosthesis is restored to its initial position. Thus, even in patients with impaired and/or weakened ligaments a natural kinematics of the joint prosthesis may be achieved. The ligament stability may in said case be complemented, compensated and/or optimized by means of adjustable spring constants of the elastically deformable element, thereby enabling an adaptation to the weight, level of activity and existing ligaments of the patient.

The elastically deformable element may be used moreover to compensate a defective position of the second bone, which is supported at least indirectly on the second component, relative to the bearing surfaces of the second component. Such a defective position may arise as a result of a defective position of the first bone relative to the second bone or because of the tolerance existing at the time of the operation. For example, the usual defective axial position is in the region of several millimetres. Said defective joint alignment leads to higher shearing forces and increased lateral abrasion of the joint prosthesis and to asymmetric loading of the collateral ligaments. Said defective joint alignment is cancelled out and/or compensated by the joint prosthesis according to the invention by means of the elastically deformable element.

It is advantageous that the elastically deformable element of the connection element is fastened to the second component, wherein the second component has a recess, which receives the elastically deformable element of the connection element. The result is on the one hand a more compact construction and on the other hand that, even when the joint prosthesis has already been implanted into the relevant bones, because the second component is not connected to either of the bones an individual adaptation is still possible through selection of a suitable elastically deformable element.

It is further advantageous that the elastically deformable element of the connection element enables a rotational excursion of the first component relative to the second component from an initial rotational position, wherein upon a rotational excursion of the first component the elastically deformable element generates a torque acting upon the first component in order to restore the first component to the initial rotational position. Thus, not only the translational motion but also the rotational motion of the joint prosthesis may be limited by means of the elastically deformable element through generation of the restoring force in the direction of the initial rotational position. In said case, as in the case of the translational motion, a stop leading to an abrupt halt is avoided, so that an extensive adaptation to the natural sequence of motion of the joint replaced by the joint prosthesis is possible, even in the event of weakened or damaged ligaments.

In an advantageous manner the elastically deformable element is formed by a multiple-bend spring leaf. Thus, both with regard to the translational motion and with regard to the rotational motion a restoring force may be generated, which is approximately proportional to the excursion and/or to the rotational excursion of the first component relative to the second component starting from the initial position and/or initial rotational position. Through selection of the bends of the spring leaf the ratio of the restoring force in anterior-posterior direction and medial-lateral direction may be preselected, wherein the dependence of the restoring force upon the rotational excursion may also be adjusted. It is however also possible for the restoring force to be superproportional to the excursion, in particular to be determined by means of a parabolic function or a higher even-order function. The excursion is in said case advantageously limited by means of an additional stop in order to limit the maximum restoring force and the tension and extension of the elastically deformable element, thereby prolonging the life of the elastic material since cycle fatigue and/or tensile and/or compressive overload is avoided.

It is advantageous that the connection element engages into the first component, thereby forming a bearing which enables rotation of the second component relative to the first component. By said means an ability to rotate freely may be provided, should the ligaments guarantee adequate support in said respect, although support in anterior-posterior and/or medial-lateral direction is still required.

In an advantageous manner the connection element in said case comprises a connection pin, which engages into a bore provided in the first component, thereby forming the bearing between the first component and the second component. The result is a simple bearing structure, which has the advantage that for the first component of the joint prosthesis a standard component is usable.

In an advantageous manner the connection pin is connected in a middle portion of the spring leaf to the spring leaf. By said means a uniform loading of the spring leaf is achieved upon an excursion of the first component.

In an advantageous manner the elastically deformable element has a cutout, into which a connection pin connected to the first component engages, wherein the cutout of the elastically deformable element is of an at least substantially X-shaped construction. Thus, the restoring force arising as a result of the excursion of the first component in anterior-posterior direction is at least substantially independent of the restoring force arising as a result of the excursion in medial-lateral direction, even when an excursion occurs in anterior-posterior direction and in medial-lateral direction.

It is advantageous that the connection pin has an at least substantially rectangular or oval cross section. Thus, the elastically deformable element, which has the preferably substantially X-shaped cutout, may upon a rotational excursion of the first component generate a torque for restoring the first component to the initial rotational position, which torque may be influenced by the length and width of the rectangular cross section.

In an advantageous manner the elastically deformable element is more easily deformable in anterior-posterior direction than in medial-lateral direction. This achieves an adaptation to the natural sequence of motion of the joint, which is to be replaced by the joint prosthesis and in which the mobility in anterior-posterior direction is greater than the mobility in medial-lateral direction.

Figure 2:
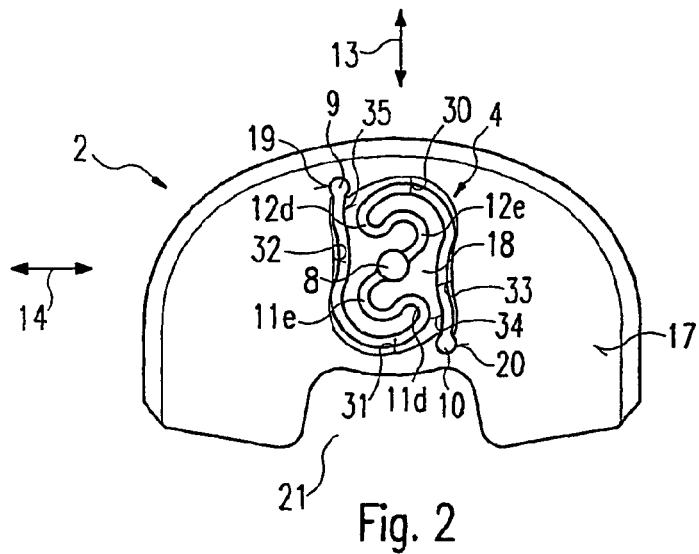
Figure 3:
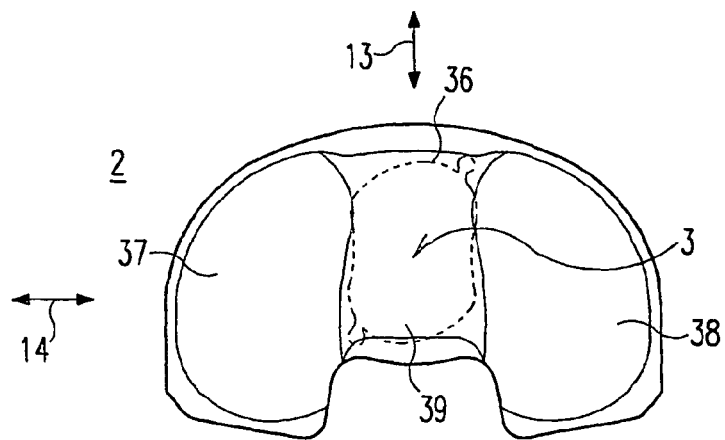
Figure 4:
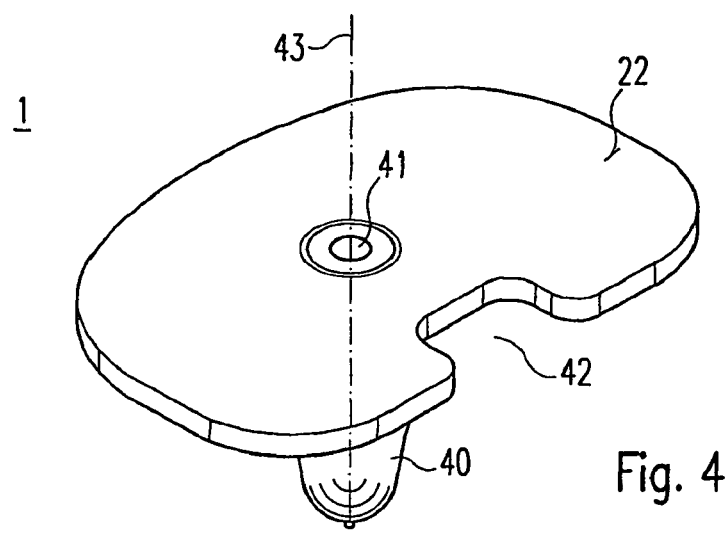
Figure 8:
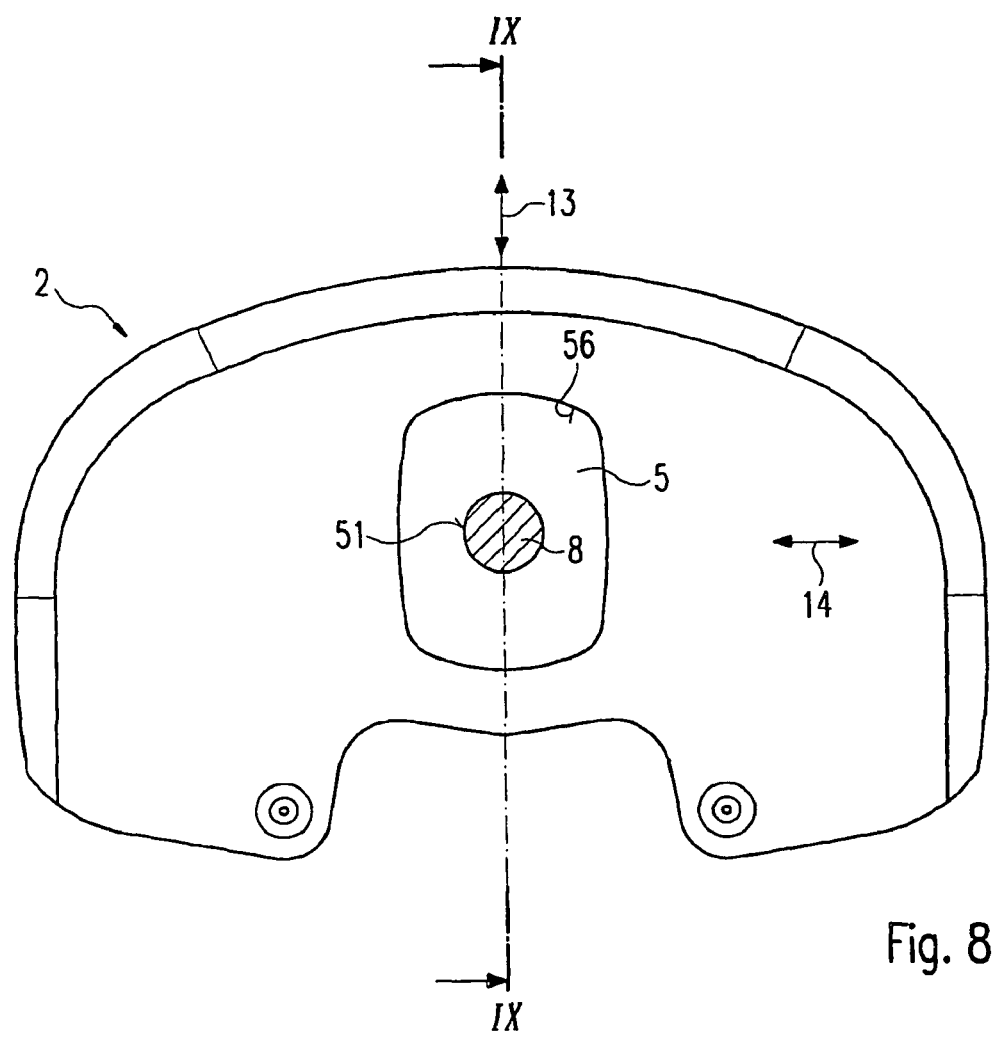
Figure 5:
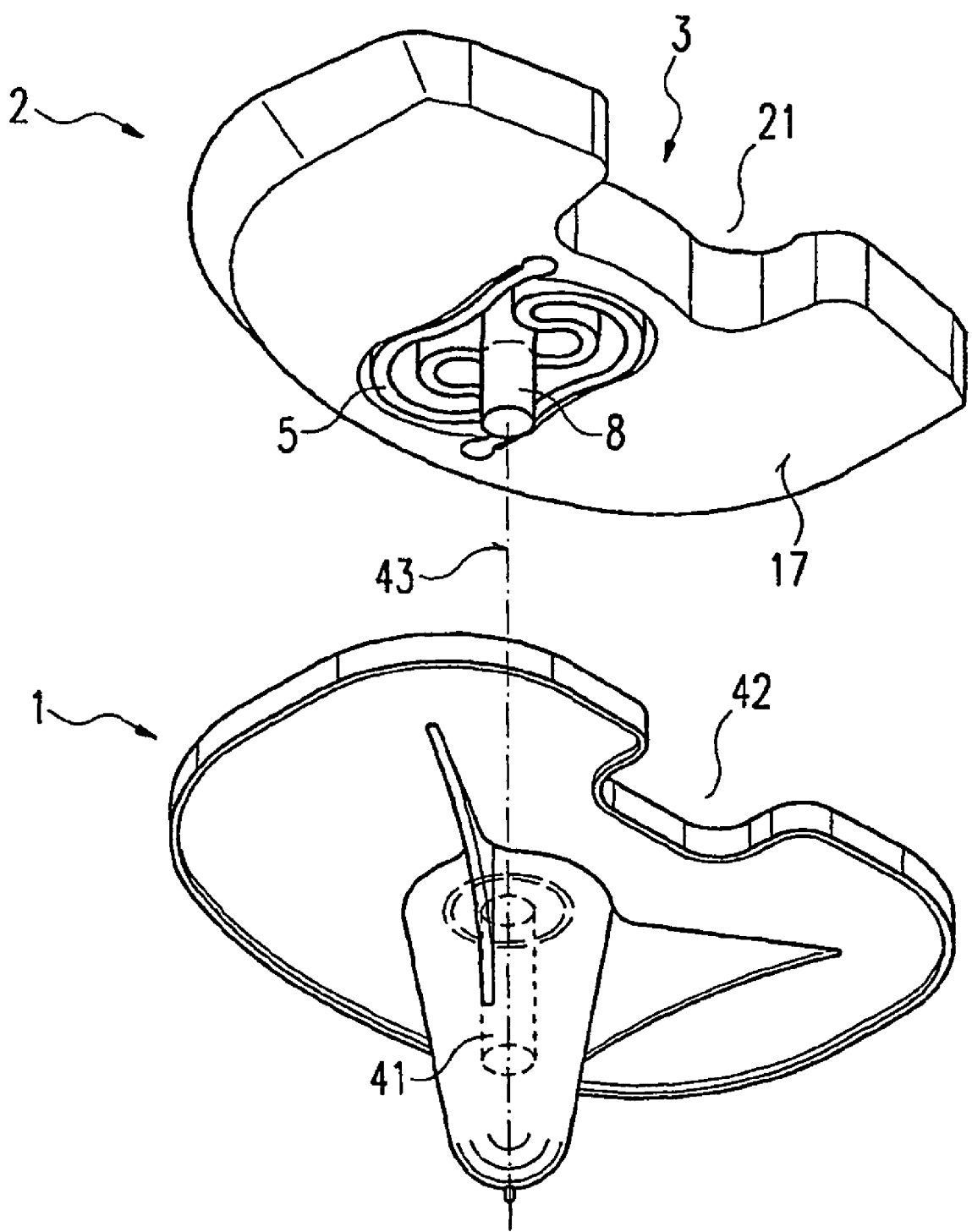
Figure 6:
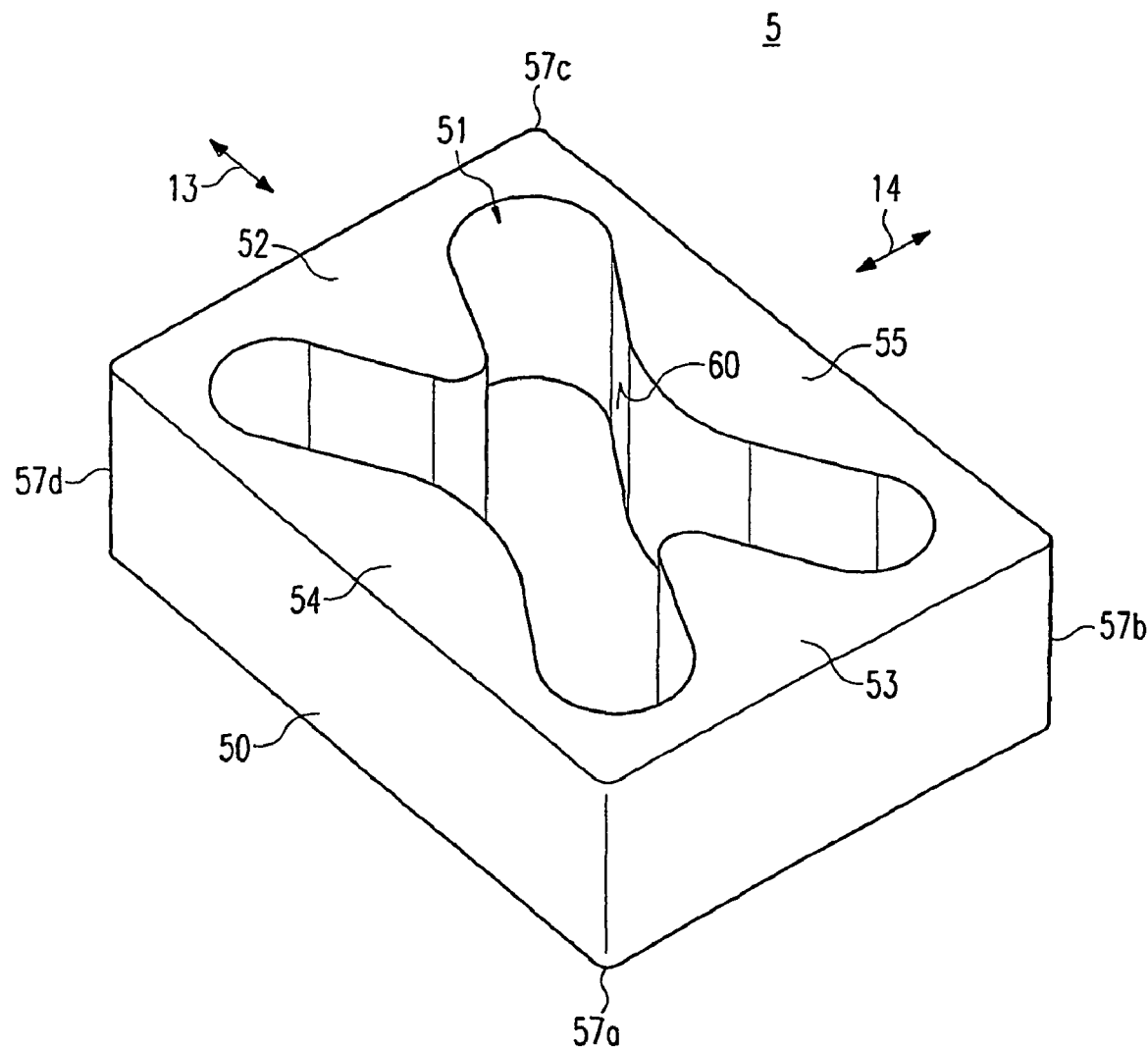
Figure 7A:
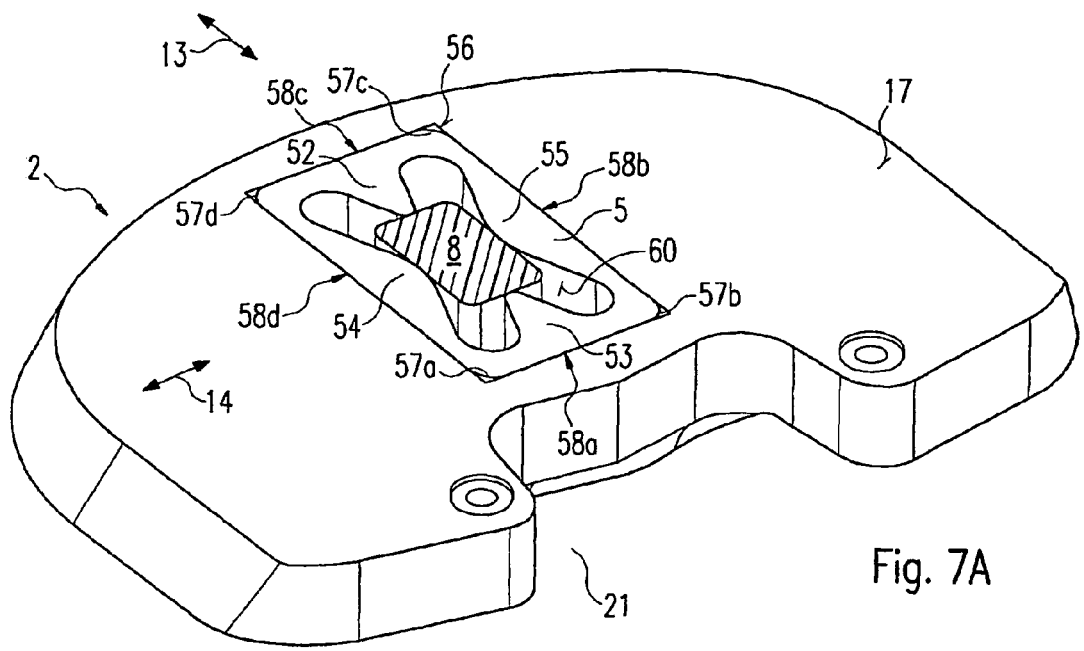
Figure 7B:
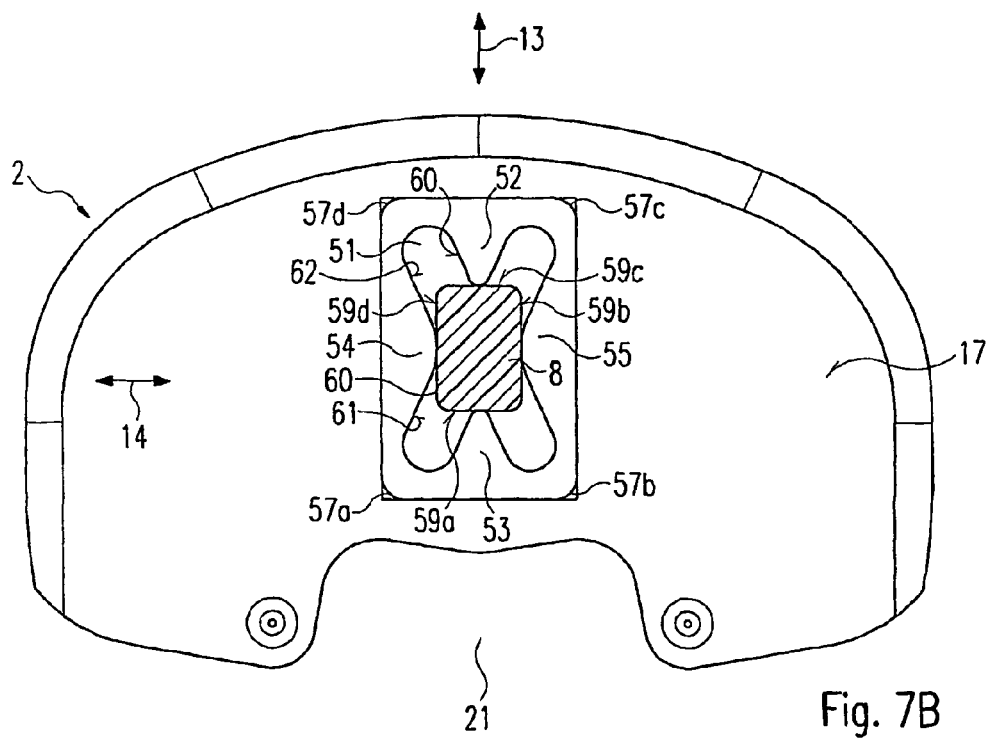
Figure 9:
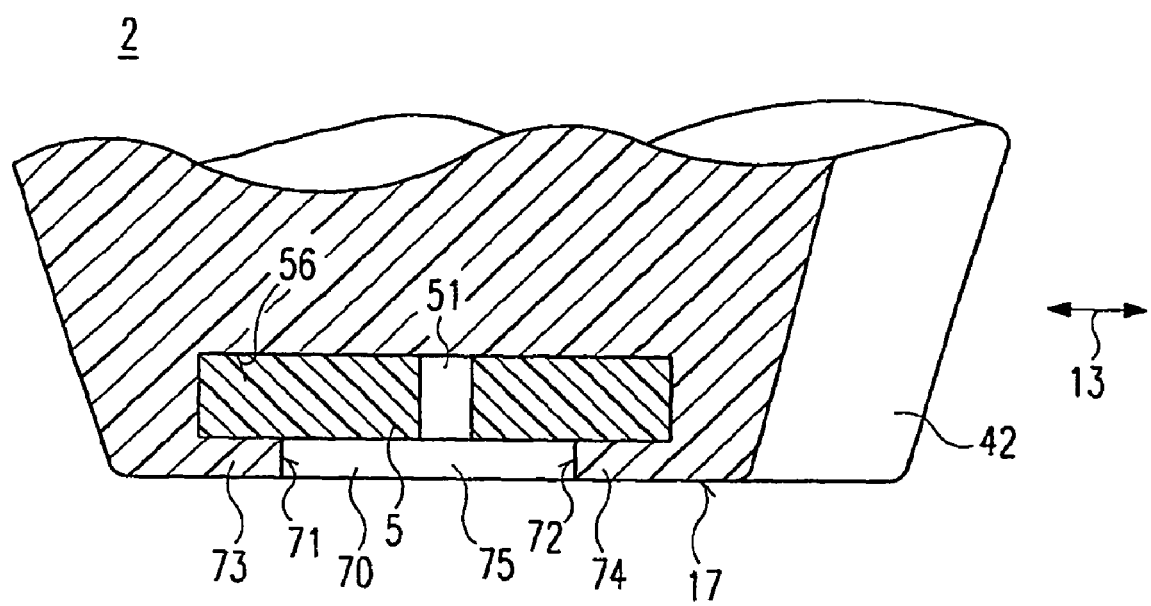

There now follows a detailed description of embodiments of the invention with reference to the drawings. The drawings show:

FIG. 1A a connection element of a joint prosthesis according to a first embodiment, which comprises an elastically deformable element formed by a multiple-bend spring leaf;

FIG. 1B a side view of the connection element illustrated in FIG. 1A;

FIG. 2 a second component of the joint prosthesis according to the first embodiment, into which the connection element illustrated in FIGS. 1a and 1b is inserted;

FIG. 3 a plan view of the second component illustrated in FIG. 2;

FIG. 4 a perspective view of a first component of the joint prosthesis according to the first embodiment;

FIG. 5 the second component illustrated in FIG. 2 prior to insertion into the first component illustrated in FIG. 4;

FIG. 6 an elastically deformable element of a connection element of a joint prosthesis according to a second embodiment;

FIG. 7A a perspective view of a second component of the joint prosthesis according to the second embodiment;

FIG. 7B a plan view of the second component illustrated in FIG. 7A;

FIG. 8 a second component of a joint prosthesis according to a third embodiment; and FIG. 9 the section denoted by IX in FIG. 8 according to a fourth embodiment of the invention.

FIG. 5 shows a first component 1 and a second component 2 according to a first embodiment of the invention, which together form the basic parts of a joint prosthesis. The first component 1 of the joint prosthesis is connected at least indirectly to a first bone, e.g. in that the first bone is severed at a specific height and optionally scraped out and the first component 1 is introduced and wedged into the resulting cavity. The second component 2 at its upper side 3, which is shown in FIG. 3, has one or more bearing shells, on which a second bone is supported preferably by means of one or more support means. The described joint prosthesis is used in particular as a knee joint prosthesis, i.e. to establish an articulated connection between tibia, as the first bone, and femur, as the second bone. The joint prosthesis according to the invention is particularly suitable for replacement of a joint, in which the ligaments have been weakened or damaged. The joint prosthesis, when used as a knee joint prosthesis, especially in the case of a weakened or damaged cruciate ligament limits the excursion of the second component 2 relative to the first component 1, particularly in anterior-posterior direction, to the natural amount, wherein a uniform displacement is achieved and a displacement of the second component 2 relative to the first component like a drawer, i.e. with no resistance between the two end positions, is avoided. The joint prosthesis is however also suitable for other applications.

FIGS. 1A and 1B show a connection element 4 of a joint prosthesis according to a first embodiment of the invention. In said case, FIG. 1B shows a side view of the connection element 4 from the direction denoted by 1B in FIG. 1A. The connection element 4 comprises an elastically deformable element 5, which is formed by a multiple-bend spring leaf. The elastically deformable element 5 comprises a first portion 6 and a second portion 7, which are at least substantially identical in length. The first portion 6 and the second portion 7 of the elastically deformable element 5 are connected by a connection pin 8, which is therefore provided in a middle portion of the elastically deformable element 5 formed by the spring leaf. On the end of the first portion 6 of the elastically deformable element 5 a first end element 9 is provided. On the end of the second portion 7 of the elastically deformable element 5 a second end element 10 is provided.

The first end element 9 and the second end element 10 are used to fasten the connection element 4 to the second component of the joint prosthesis in the manner described with reference to FIG. 2. The connection pin 8 is used to connect the second component 2—which is connected by the end elements 9, 10 to the connection element 4—of the joint prosthesis to the first component 1 of the joint prosthesis in the manner described with reference to FIGS. 4 and 5.

The first portion 6 of the elastically deformable element 5 of the connection element 4 has bending points 11*a* to 11*d*. In a corresponding manner the second portion 7 of the elastically deformable element 5 also has a plurality of bending points 12*a* to 12*b*. In the present embodiment the first portion 6 and the second portion 7 are constructed so as to be, in relation to the connection pin 8, at least substantially symmetrical to one another. In relation to the connection pin 8 the first end element 9 is therefore disposed at least substantially opposite the second end element 10. In a corresponding manner, in relation to the connection pin 8 the bending point 11*a* is disposed opposite the bending point 12*a*, the bending point 11*b* opposite the bending point 12*b*, and so on, and the bending point 11*e* opposite the bending point 12*e*. Given fixed end elements 9, 10, therefore, upon an excursion of the connection pin 8 from the initial position illustrated in FIG. 1A in anterior-posterior direction 13 and/or in medial-lateral direction 14 in each case a symmetrical deformation of the elastically deformable element 5 of the connection element 4 in the form of a spring leaf occurs and results in a restoring force for restoring to the initial position, wherein excursions symmetrical in relation to the connection pin 8 result in restoring forces of equal magnitude.

By virtue of the number and arrangement of the bending points 11*a* to 11*e* and 12*a* to 12*e*, wherein optionally a higher or lower number of bending points may be provided, the elasticity of the elastically deformable element 5 may in dependence upon the excursion, which is composed of an excursion in anterior-posterior direction 13 and an excursion in medial-lateral direction 14, within specific limits define the restoring force needed for the respective application of the joint prosthesis.

What is more, a desired torque, which given fixed end elements 9, 10 is generated upon a rotational excursion of the connection pin 8 from the initial rotational position shown in FIG. 1A, may also be defined by virtue of the arrangement of the bending points 11*a* to 11*e* and 12*a* to 12*e* and in particular by virtue of the number of reverse bends.

By virtue of the connection element 4 according to the invention it is therefore possible to achieve two primary effects, which may each be used individually but also in combination. On the one hand, given fixed end elements 9, 10 upon a translational excursion of the connection pin 8 from the initial position shown in FIG. 1A, i.e. upon an excursion which may be broken down into a fraction in anterior-posterior direction 13 and a fraction in medial-lateral direction 14, a restoring force is generated, as a result of which the connection pin 8 is restored to the initial position shown in FIG. 1A. On the other hand, upon a rotational excursion of the connection pin 8 of the connection element 4, i.e. upon twisting of the connection pin 8 about its axis of symmetry 15, a torque is generated, as a result of which the elastically deformable element 5 is returned to the initial position shown in FIG. 1*a*. In the case of the rotational excursion, it is advantageous that at least the upper portion 16 of the elastically deformable element 5 has a polygonal, in particular square cross section in order to enable advantageous, in particular non-slip interaction with a suitable mating part.

In FIG. 2 the second component of the joint prosthesis according to the first embodiment of the invention is illustrated, into which the connection element 4 shown in FIGS. 1A and 1B is inserted. Elements that have already been described are provided, in this and all of the other drawings, with matching reference characters so as to avoid repeat description.

The second component 2 has a flat underside 17. The second component 2 is moreover provided with a cutout 18, which is open at least in the direction of the flat underside 17. Said opening in the direction of the flat underside 17 is necessary at least in the region of the connection pin 8 but may—unlike in the first embodiment shown in FIG. 2—otherwise be entirely or partially closed.

The cutout 18 comprises a first recess 19 and a second recess 20, which are used to receive the first end element 9 and the second end element 10 of the elastically deformable element 5 of the connection element 4, wherein the first recess 19 and the first end element 9 and/or the second recess 20 and the second end element 10 are of a mutually adapted design. Thus, the end elements 9, 10 are fixed relative to the second component 2. The displacement of the connection pin 8 given fixed end elements 9, 10, which was discussed with reference to FIGS. 1A and 1B, is therefore synonymous with a displacement of the connection pin 8 relative to the second component 2 from the initial position shown in FIG. 2. The same applies to a twisting of the connection pin 8 relative to the second component 2.

The second component 2 has a cutout 21, which is used to receive ligaments. Given the use of the joint prosthesis as a knee joint prosthesis, the cutout 21 is used to receive the posterior cruciate ligament, if the latter is still present.

The connection element 4 is introduced fully into the cutout 18, in particular so as not to project beyond a plane defined by the flat underside 17. This prevents damage to the tibia bearing surface 22 of the first component 1, which surface lies opposite the flat underside 17 of the second component 2 and is shown in FIG. 4, and prevents impairment of the action of the elastically deformable element 5.

The cutout 18 of the second component 2 has an anterior stop face 30 and a posterior stop face 31. A first lateral stop face 32 and a second lateral stop face 33 are moreover provided in the cutout 18. Depending on the side of the body, at which the joint prosthesis is used, the first lateral stop face 32 is disposed medially or laterally, while the second lateral stop face 33 is then disposed at the other side (laterally or medially).

The anterior stop face 30 and the posterior stop face 31 effect a limitation of the excursion of the connection pin 8 in anterior-posterior direction 13, wherein, because a more extreme excursion in anterior-posterior direction 13 leads to abutment of the second portion 7 at the bending point 12*c* with the anterior stop face 30 and/or of the first portion 6 at the bending point 11*c* with the posterior stop face 31, a steeper increase of the restoring force occurs with progressive excursion. In medial-lateral direction 14, because of the multiple reverse bends defined by the bending points 11*d*, 11*e*, 12*d*, 12*e*, an excursion of the connection pin 8 leads initially only to generation of a restoring force of less magnitude, which however increases steeply in the event of abutment of the first portion 6 of the elastically deformable element 5 at its bending point 11*d* with the inner face 34 of the second portion 7 supported against the second lateral stop face 33 or in the event of abutment of the second portion 7 at its bending point 12*d* with the inner face 35 of the first portion 6 supported against the first lateral stop face 32.

An increase of the torque, which arises upon a rotational excursion and counteracts the rotational excursion, occurs in a corresponding manner. In said case, this leads, in the one direction, to abutment of the bending point 11*e* with the inner face 35 of the first portion 6 of the elastically deformable element 5 and/or (depending on additional excursion in medial-lateral direction 14) of the bending point 12*e* with the inner face 34 of the second portion 7 of the elastically deformable element 5 and, in the other direction, to abutment of the bending point 12*d* with the inner face 35 of the first portion 6 of the elastically deformable element 5 and/or of the bending point lid with the inner face 34 of the second portion 7 of the elastically deformable element 5.

Thus, in the connection element 4 described with reference to FIG. 2 and inserted into the cutout 18 of the second component 2, extreme excursions and/or extreme rotational excursions lead to a steep increase of the restoring force, resulting in a limitation of the motion. The limits of said motion may in said case be defined structurally by the size of the cutout 18 of the second component 2 and by the connection element 4, in particular by the arrangement of the bending points 11*a* to 11*e* and 12*a* to 12*e*.

FIG. 3 shows the second component 2 illustrated in FIG. 2 from the opposite side. Here, the arrangement of the cutout 18 is shown as a discontinuous line 36 in FIG. 3. For the non-illustrated situation where the cutout 18 takes the form of a through-opening, the discontinuous line 36 indicates the edge of the through-opening.

The upper side 3 of the second component 2 has the bearing shells 37, 38, into which a support means connected to the second bone engages in order to support the second bone. The support means in said case rolls in the bearing shells 37, 38 preferably in anterior-posterior direction 13, while being guided in medial-lateral direction 14 by the bearing shells 37, 38 and optionally also by the middle piece 39 of the second component 2.

FIG. 4 shows a perspective view of the first component 1. The first component 1 has a fixating pin 40, which is used to fix the first component 1 in a first bone. The first component 1 moreover has a tibia bearing surface 22, on which the second component 2 is supported by its flat underside 17. For connecting the second component 2 to the first component 1 by means of the connection element 4 a bore 41 is provided in the first component 1. The connection pin 8 is introduced into the bore 41, thereby enabling the second component to rotate freely relative to the first component. The bore 41 may however also take the form of an opening having a polygonal, in particular square cross section, so that the suitably adapted connection pin 8 latches into the opening 41 and the rotational excursion of the second component relative to the first component is limited in accordance with the mode of operation described with reference to FIGS. 1A, 1B and 2.

The cutout 42 provided in the first component 1, like the cutout 21 of the second component 2, is used to receive ligaments, in particular given the use of the joint prosthesis as a knee joint prosthesis to receive the posterior cruciate ligament.

To assemble the joint prosthesis the second component 2, into which the connection element 4 has been introduced, is moved along the axis 43 onto the first component 1 so that the connection pin 8 engages into the bore 41 in the manner shown in FIG. 5.

FIG. 6 shows an elastically deformable element 5 of a joint prosthesis according to a second embodiment. The elastically deformable element 5 comprises an at least substantially cuboidal basic body 50, into which an at least substantially X-shaped cutout 51 is introduced, wherein the cutout 51 takes the form of a through-opening. The elastically deformable element 5 in this embodiment is of an at least substantially symmetrical construction, there being in particular a symmetry in anterior-posterior direction 13 and a symmetry in medial-lateral direction 14. For specific applications, the elastically deformable element 5 may however also be of an asymmetrical construction by designing the cutout 51 asymmetrically and/or manufacturing the elastically deformable element 5 from materials having different moduli of elasticity. For example, the anterior region 52 may be of a different construction to the posterior region 53 and/or the first lateral region 54 may be of a different construction to the second lateral region 55. In the second embodiment illustrated in FIG. 6 there is an asymmetry with regard to the anterior-posterior direction 13 and the medial-lateral direction 14 because the length of the basic body 50 in anterior-posterior direction 13 is greater than the width of the basic body 50 in medial-lateral direction 14 and accordingly the X-shaped cutout 51 is also elongated in anterior-posterior direction 13. The result of this is that, upon a displacement—described in greater detail with reference to FIGS. 7A and 7B—of the second component 2 relative to the first component 1, given identical excursion a stronger restoring force is generated in medial-lateral direction 14 than in anterior-posterior direction 13.

FIG. 7A shows the second component 2, into which the elastically deformable element 5 is inserted. For insertion of the elastically deformable element 5 into the second component 2 a cutout 56 is provided in the second component 2 and is open in the direction of the flat underside 17 of the second component 2. To facilitate introduction of the elastically deformable element 5 into the cutout 56, the elastically deformable element 5 has rounded-off edges 57*a* to 57*d*. The opening of the cutout 56 towards the flat underside 17 need not necessarily be fully open, it being in particular advantageous for fastening of the elastically deformable element 5 in the cutout 56 when in the assembled state the flat underside 17 projects slightly over the elastically deformable element in the edge regions 58*a* to 58*d*.

In FIG. 7A a connection pin 8 is shown in a sectional view, wherein the section is effected along the plane lying in the flat underside 17. The connection pin 8 is connected to the first component 1, wherein it may also be constructed integrally with the first component 1. By virtue of the engagement of the connection pin 8 into the elastically deformable element 5 both the translational and the rotational mobility of the second component relative to the first component is limited. In anterior-posterior direction 13 this is effected by compression of the anterior region 52 and/or of the posterior region 53 of the elastically deformable element 5. In medial-lateral direction 14 the limitation of the mobility is effected by compression of the first lateral region 54 and/or of the second lateral region 55 of the elastically deformable element 5. Thus, upon an excursion of the first component 1 relative to the second component 2 from an initial position, through compression of the anterior region 52 or posterior region 53 and/or of the first lateral region 54 or second lateral region 55 of the elastically deformable element 5 a restoring force is generated for restoring the first component to the initial position illustrated in FIG. 7A.

Upon a rotational excursion of the first component 1, which corresponds to a rotational excursion of the connection pin 8, an elastic deformation of the said regions 52 to 55 is achieved and gives rise to a torque that produces the restoring of the first component 1 to the initial rotational position shown in FIG. 7A.

In said case, the lateral faces 59a to 59d interact with the inner face 60 of the X-shaped cutout 51, wherein in an extreme rotational position, for example, the part 60 of the lateral face 59d fully abuts the part 61 of the inner face 60 of the cutout 51, leading to a steeper increase of the restoring force, so that in the second embodiment of the joint prosthesis also a limitation of the rotational excursion is provided.

A limitation of the translational excursion of the first component 1 relative to the second component 2 in anterior-posterior direction 13 and/or in medial-lateral direction 14 is effected likewise through full abutment of the appropriate lateral face 59a to 59d with the inner face 60, e.g. when the connection pin 8 with the lateral face 59d compresses the first lateral region 54 in such a way that the lateral face 59d at least substantially fully abuts the parts 61, 62 of the inner face 60.

In FIG. 8 a second component 2 of a joint prosthesis according to a third embodiment is shown, into which an elastically deformable element 5 is introduced. The elastically deformable element 5 in said case has a cutout 51, which is adapted in shape and size to the connection pin 8, which is connected to the first component 1 and is shown in section in FIG. 8. According to this embodiment a restoring force is generated, which builds up uniformly in relation to the excursion, wherein the translational mobility is considerably reduced compared to the first and the second embodiment. The joint prosthesis according to the third embodiment is therefore particularly suitable for replacing joints, in which the associated ligaments are considerably weakened or highly impaired. The connection pin 8 may in said case also be rotatable relative to the first component 1. Furthermore, the connection pin 8 may also be locked against rotation relative to the elastically deformable element 5 by means of a different shape, in particular by means of an oval or polygonal shape.

FIG. 9 shows the section, denoted by IX in FIG. 8, according to a fourth embodiment of the invention. In this embodiment the elastically deformable element 5 is introduced into a cutout 56, which is only partially open towards the underside 17 of the second component 2. The opening 70 therefore has a smaller cross section than the elastically deformable element 5. The elastically deformable element 5 has a cutout 51, into which a connection pin may be introduced. Upon a movement of the connection pin in anterior-posterior direction 13 and/or medial-lateral direction 14, the displacement is limited by virtue of the connection pin striking against the stop-and/or boundary faces 71, 72, which are formed on the second component 2 in the region of the opening 70, with the result that the compression of the elastically deformable element 5 is protected against overload because the maximum compression of the elastically deformable element 5 is limited. In the illustrated embodiment the boundary face 71 is formed on the stop 73 and the boundary face 72 is formed on the stop 74. The stop face 72, 73 are in said case part of a surface area 75 peripherally delimiting the opening 70.

The second component of the joint prosthesis described according to the various embodiments is preferably made of ceramic material or of polyethylene, in particular UHMW polyethylene, cross-linked polyethylene or PEEK (polyetherether ketone). The elastically deformable element 5 of the joint prosthesis according to embodiment 2 and/or 3 is preferably made of a non-rigid material, such as an elastomer, in particular rubber, polyurethane, silicone or silicone polycarbonate urethane. In the first embodiment, it is preferably made of a polymer or a metal, in particular spring steel. The connection pin 8, if it is constructed integrally with the elastically deformable element 5, is preferably made of the same material as the elastically deformable element 5 of the connection element 4. Otherwise, it is also possible for the connection pin 8 to be made of a hard material, such as a metal, in particular a CoCr alloy, steel or a polymer. The first component 1 of the joint prosthesis is preferably likewise made of one of the stated hard materials.

The invention is not restricted to the described embodiments.

The invention claimed is:

1. A joint prosthesis, in particular a knee joint prosthesis for establishing an articulated connection between a first bone and at least one second bone of a patient, said prosthesis comprising a first component, which is at least indirectly connectable to the first bone, at least one second component, on which the second bone is at least indirectly supportable and which is movably mountable on at least one bearing surface of the first component, a connection element connecting the first component to the second component, said connection element comprising at least one elastically deformable element consisting of a multiple-bend leaf spring enabling an excursion of the first component relative to the second component from an initial position, wherein upon the excursion of the first component the elastically deformable element generates a restoring force acting upon the first component to restore the first component to the initial position thereof; the connection element further comprising a connection pin engaging into a bore which is provided in the first component to thereby form a bearing between the first component and the second component, and wherein the connection pin is connected to said multiple-bend leaf spring in a middle portion of the leaf spring.

2. A joint prosthesis according to claim 1, wherein said elastically defendable element is fastened to the second component.

3. A joint prosthesis according to claim 2, wherein the second component has a cutout which receives the elastically deformable element.

4. A joint prosthesis according to claim 1, wherein the elastically deformable element enables a rotational excursion of the first component relative to the second component from an initial rotational position, whereby upon a rotational excursion of the first component the elastically deformable element generates a torque acting upon the first component to restore the first component to the initial rotational position.

5. A joint prosthesis according to claim 1, wherein the connection element engages into the first component so as to form the bearing which enables rotation of the second component relative to the first component.

6. A joint prosthesis according to claim 1, wherein the leaf spring is selected from the group of materials consisting of an elastically deformable plastic material or metal.

* * * * *